US012678063B2

(12) United States Patent
Marutani et al.

(10) Patent No.: US 12,678,063 B2
(45) Date of Patent: Jul. 14, 2026

(54) PULSE WAVE ESTIMATING DEVICE AND PULSE WAVE ESTIMATION METHOD

(71) Applicant: Mitsubishi Electric Corporation, Tokyo (JP)

(72) Inventors: Takafumi Marutani, Tokyo (JP); Ryohei Murachi, Tokyo (JP); Yudai Nakamura, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 6 days.

(21) Appl. No.: 18/630,757

(22) Filed: Apr. 9, 2024

(65) Prior Publication Data

US 2024/0423490 A1      Dec. 26, 2024

(30) Foreign Application Priority Data

Jun. 26, 2023    (JP) ................................. 2023-103835

(51) Int. Cl.
A61B 5/024 (2006.01)
(52) U.S. Cl.
CPC ................................. A61B 5/02416 (2013.01)
(58) Field of Classification Search
CPC ........................... A61B 5/02416; A61B 5/0077
See application file for complete search history.

(56) References Cited

U.S. PATENT DOCUMENTS

2005/0195317 A1*  9/2005  Myoga ................... H04N 23/74
                                                    348/370
2008/0075382 A1*  3/2008  Sugeno ................ H04N 23/745
                                                    348/E5.041
2014/0221848 A1*  8/2014  Nagasaka .............. A61B 5/681
                                                    600/479
2018/0055364 A1*  3/2018  Pierro ................ A61B 5/02125
2021/0121083 A1*  4/2021  Edo ...................... A61B 5/0077
2021/0186346 A1*  6/2021  Nakamura ......... A61B 5/02108
2023/0290186 A1*  9/2023  Kaneko .................. G06V 40/40
2023/0359717 A1* 11/2023  Nakazaki .............. A61B 5/107

OTHER PUBLICATIONS

Kumar et al., "DistancePPG: Robust non-contact vital signs monitoring using a camera", Biomedical Optics Express, 2015, vol. 6, No. 5, DOI: 10.1364/BOE.6.001565, total 24 pages.

* cited by examiner

*Primary Examiner* — Hien N Nguyen
(74) *Attorney, Agent, or Firm* — Birch, Stewart, Kolasch & Birch, LLP

(57)      ABSTRACT

A pulse wave estimating device includes processing circuitry configured to; acquire a captured image of a human; detect a skin region of the human on the captured image; set, as a plurality of measurement regions for extracting luminance signals representing luminance changes, regions formed by dividing the skin region on the captured image in a predetermined manner; extract the luminance signals on a basis of the luminance changes in the measurement regions on the captured image; and estimate a pulse wave of the human on a basis of the extracted luminance signals; perform measurement region resetting, when a ratio of measurement regions, in which the number of pixels is equal to or greater than a preset reference value among the set plurality of measurement regions, is lower than a threshold, in such a manner as to make the ratio of measurement regions equal to or higher than the threshold.

9 Claims, 8 Drawing Sheets

FIG. 7A
FIG. 7B
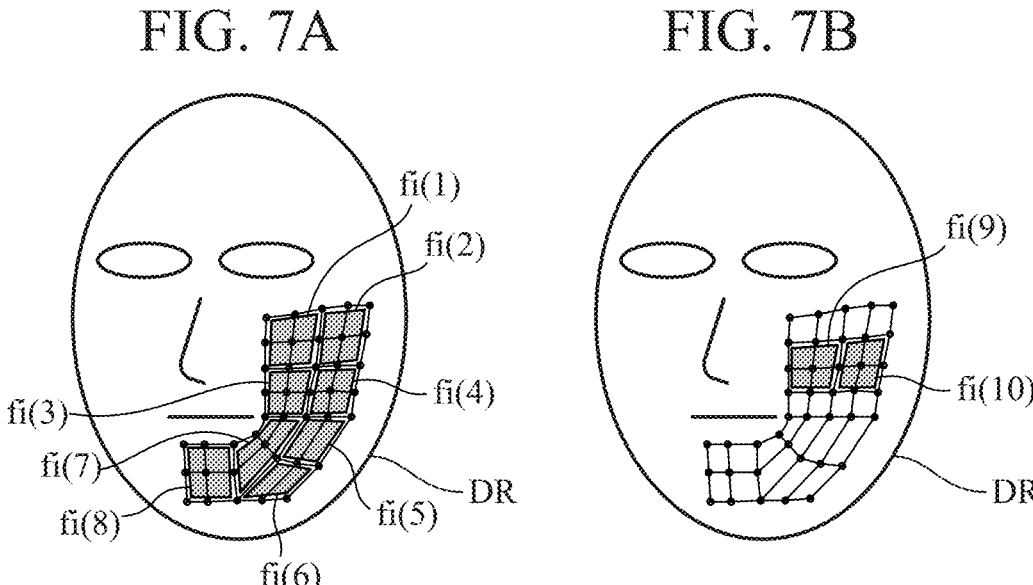
FIG. 7C
FIG. 7D
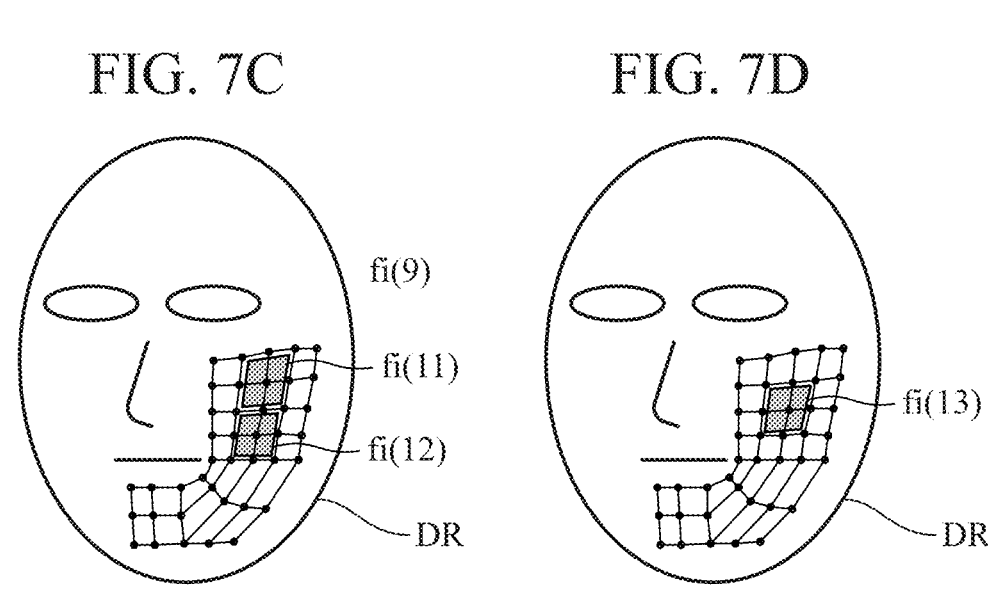

PULSE WAVE ESTIMATING DEVICE AND PULSE WAVE ESTIMATION METHOD

TECHNICAL FIELD

The present disclosure relates to a pulse wave estimating device and a pulse wave estimation method.

BACKGROUND ART

As a technique of estimating pulse waves of a subject in a non-contact manner without placing a burden on the subject, there is a technique in which images of the face of the subject are captured with a camera, and the pulse waves are estimated from a minute change in luminance on the face surface of the subject (e.g. Non-Patent Literature 1). In this technique, for example, a plurality of measurement regions is set on the facial images of the subject, and a frequency power spectrum of a luminance signal acquired from each set measurement region is calculated. Then, a pulse wave of the subject is estimated from a peak frequency of the frequency power spectrum calculated for each measurement region. In addition, the estimated pulse waves are synthesized, and a pulse rate is also estimated from a peak of a frequency power spectrum of a pulse wave obtained by the synthesis.

CITATION LIST

Patent Literature

Non-Patent Literature 1: Mayank Kumar, et al., "DistancePPG: Robust non-contact vital signs monitoring using a camera," Biomedical optics express, 6 (5), 1565-1588, 2015

SUMMARY OF INVENTION

Technical Problem

However, there has been a problem with the technique described above that deterioration of the image resolution of captured images of the subject due to a change of the installation layout of a camera or the like leads to deterioration of the resolving power, and to deterioration of the pulse wave estimation precision.

The present disclosure has been made to solve the problem described above, and an object thereof is to obtain a pulse wave estimating device that can suppress deterioration of the pulse wave estimation precision.

Solution to Problem

A pulse wave estimating device according to the present disclosure includes: processing circuitry configured to; acquire a captured image of a human; detect a skin region of the human on the captured image; set, as a plurality of measurement regions for extracting luminance signals representing luminance changes, regions formed by dividing the skin region on the captured image in a predetermined manner; extract the luminance signals on a basis of the luminance changes in the measurement regions on the captured image; and estimate a pulse wave of the human on a basis of the extracted luminance signals, in which the processing circuitry performs measurement region resetting, when a ratio of measurement regions, in which a number of pixels is equal to or greater than a preset reference value among the set plurality of measurement regions, is lower than a threshold, in such a manner as to make the ratio of measurement regions equal to or higher than the threshold.

Advantageous Effects of Invention

Since the present disclosure adopts the configuration as described above, it is possible to suppress deterioration of the pulse wave estimation precision.

BRIEF DESCRIPTION OF DRAWINGS

FIG. 7A, FIG. 7B, FIG. 7C and FIG. 7D are figures for explaining an example of the measurement region resetting performed by the measurement region setting unit in the first embodiment.

DESCRIPTION OF EMBODIMENTS

Hereinbelow, an embodiment is explained in detail with reference to the figures.

First Embodiment

Figure 1:
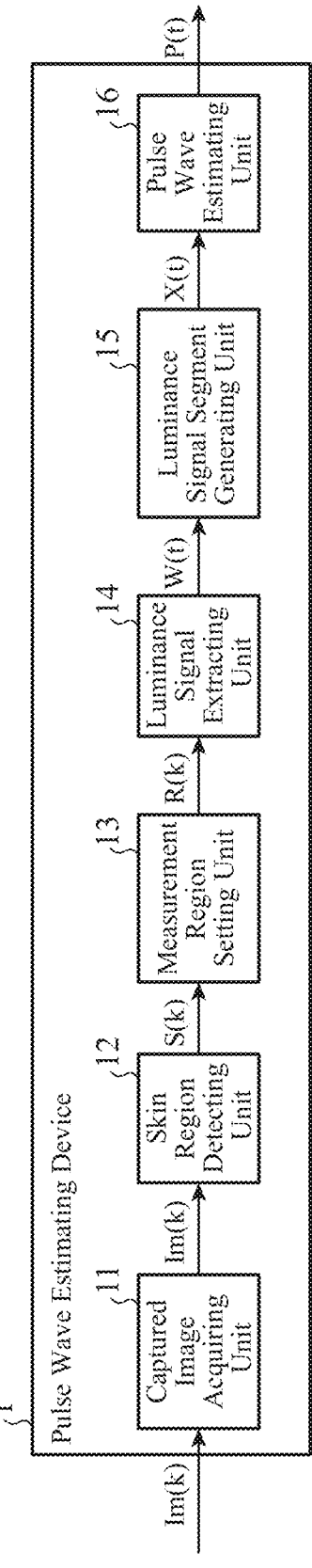
FIG. 1 is a figure depicting a configuration example of a pulse wave estimating device according to a first embodiment.

FIG. 1 is a figure depicting a configuration example of a pulse wave estimating device 1 according to a first embodiment. The pulse wave estimating device 1 estimates pulse waves of a human on the basis of captured images of the human. In the following explanation, the human whose pulse waves are to be estimated by the pulse wave estimating device 1 is also referred to as a "subject."

The pulse wave estimating device 1 acquires captured images including a series of frames Im(k) obtained by capturing images of an area where there is a skin region which is a region including at least the skin of the subject at a preset frame rate Fr. Here, k represents a frame number allocated to each frame. For example, a frame obtained at a timing next to the frame Im(k) is a frame Im(k+1). Then, the pulse wave estimating device 1 estimates pulse waves of the subject for each frame Im(k), and outputs a pulse wave estimation result P(t) which is information representing the estimated pulse wave (hereinafter, called "pulse wave information"). For example, the pulse wave information may be time-series data of the pulse waves of the subject estimated by a pulse wave estimating unit 16 mentioned later or may be a pulse rate of the subject.

Note that the number of subjects who are humans included in captured images may be one or may be more than one. For simplification of explanation, it is assumed in the following explanation that the number of subjects included in captured images is one. In addition, it is assumed in the following explanation that, as an example, the pulse wave estimating device 1 is mounted on a vehicle (an illustration of the vehicle is omitted), and the subject is the driver of the vehicle. That is, the pulse wave estimating device 1 estimates pulse waves of the driver of the vehicle.

For example, as depicted in FIG. 1, the pulse wave estimating device 1 includes a captured image acquiring unit 11, a skin region detecting unit 12, a measurement region setting unit 13, a luminance signal extracting unit 14, a luminance signal segment generating unit 15 and a pulse wave estimating unit 16.

The captured image acquiring unit 11 acquires a captured image of the subject driver. Specifically, the captured image acquiring unit 11 acquires a captured image of the driver of the vehicle captured with an image-capturing device (an illustration of the image-capturing device is omitted) mounted on the vehicle. Note that the image-capturing device is installed in such a manner that images of an area where there is a skin region of the driver can be captured. The captured image acquiring unit 11 outputs the acquired captured image to the skin region detecting unit 12.

The skin region detecting unit 12 detects a skin region of the subject driver on a frame Im(k) included in the captured image acquired by the captured image acquiring unit 11. Then, the skin region detecting unit 12 outputs information representing the detected skin region as skin region information S(k) to the measurement region setting unit 13 along with the frame Im(k) on which the skin region information S(k) has been detected.

Note that it is assumed in the following explanation that the skin region is information representing a rectangular region representing the position and size of the face of the driver on the frame Im(k). The note that the detection of the face of the driver can be implemented by using a known means. For example, the skin region detecting unit 12 can extract a rectangular region surrounding the face of the driver by using a cascade face detector using Haar-like features.

Note that the skin region may be a region corresponding to a part other than the face of the driver. For example, the skin region may be a region corresponding to a part belonging to the face such as an eye, an eyebrow, the nose, the mouth, the forehead, a cheek or the chin of the driver. In addition, the skin region may be a region corresponding to a body part other than the face such as the head, a shoulder, a hand, the neck or a leg of the driver. In addition, the skin region may be not one region, but include a plurality of regions.

The measurement region setting unit 13 acquires the frame Im(k) and the skin region information S(k) output from the skin region detecting unit 12. In addition, the measurement region setting unit 13 acquires vehicle layout information from a control device (not depicted) mounted on the vehicle. The vehicle layout information includes at least information representing the positional relationship between the image-capturing device installed on the vehicle and the driver. For example, the vehicle layout information includes: information representing the position in the vehicle where the image-capturing device is installed; information representing the orientation of the image-capturing device; information representing the position of the seat where the driver is seated relative to the position in the vehicle where the image-capturing device is installed; and the like.

On the basis of the acquired frame Im(k), skin region information S(k) and vehicle layout information described above, the measurement region setting unit 13 divides the skin region represented by the skin region information S(k) on the frame Im(k) in a predetermined manner, and sets regions obtained by the division as a plurality of measurement regions for extracting luminance signals representing luminance changes.

After setting the plurality of measurement regions, the measurement region setting unit 13 generates measurement region information R(k) representing the set plurality of measurement regions. The measurement region information R(k) includes information representing the position and size of Rn (positive integer) measurement regions on the captured image. It is assumed that the measurement regions are measurement regions fi(k) (i=1, 2, . . . , Rn). It is assumed in the first embodiment that each measurement region fi(k) is a quadrilateral, and the position and size of the measurement region fi(k) are represented by the coordinate values of the four vertices of the quadrilateral on the captured image.

Figure 2A:
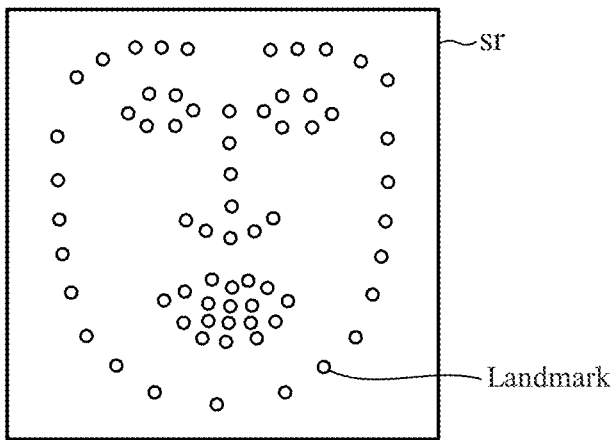
FIG. 2A, FIG. 2B and FIG. 2C are figures for explaining an example of a measurement region setting method performed by a measurement region setting unit in the first embodiment.
Figure 2B:
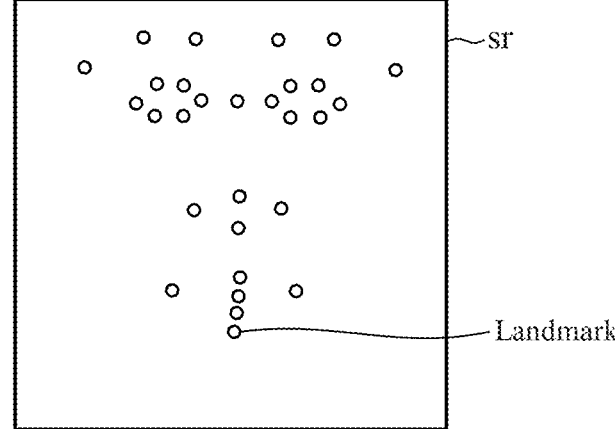
Figure 2C:
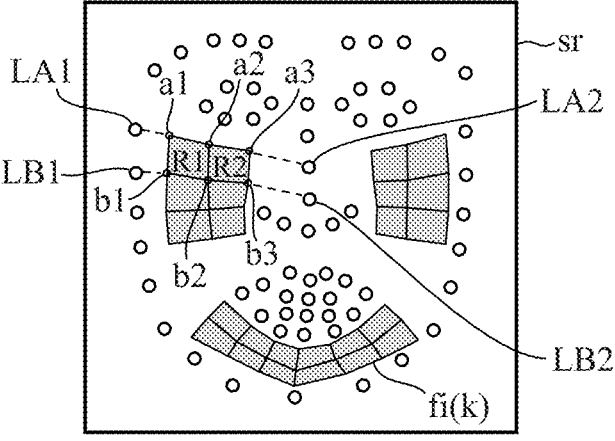

Here, FIG. 2A, FIG. 2B and FIG. 2C are figures for explaining an example of a measurement region setting method performed by the measurement region setting unit 13 in the pulse wave estimating device 1 according to the first embodiment. An example of the method performed by the measurement region setting unit 13 to set the plurality of measurement regions is explained by using FIG. 2.

First, as depicted in FIG. 2A and FIG. 2B, the measurement region setting unit 13 detects Ln (positive integer) landmarks of facial organs such as the tails of the eyes, the inner corners of the eyes, the nose or the mouth in a skin region sr represented by the skin region information S(k). In FIG. 2A and FIG. 2B, the landmarks are represented by circles. The measurement region setting unit 13 sets a vector storing the coordinate values of a detected landmark as L (k). Note that the measurement region setting unit 13 may detect facial organs by using a known means such as by using a model called Constrained Local Model (CLM).

Next, the measurement region setting unit 13 sets the vertex coordinates of the quadrilaterals of measurement regions fi(k) on the basis of detected landmarks. For example, the measurement region setting unit 13 sets vertex coordinates of quadrilaterals as depicted in FIG. 2C, and sets Rn measurement regions fi(k).

Setting of measurement regions fi(k) at a portion corresponding to a cheek in the skin region sr by the measurement region setting unit 13 is explained as an example. The measurement region setting unit 13 selects a landmark LA1 on the contour of the face and a landmark LA2 on the nose. The measurement region setting unit 13 may first select the landmark LA2 on the nose, and select the landmark LA1 on the contour of the face closest to the landmark LA2 on the nose. Then, the measurement region setting unit 13 sets auxiliary landmarks a1, a2 and a3 in such a manner that the auxiliary landmarks a1, a2 and a3 equally divide the line segment between the landmark LA1 and the landmark LA2 into four.

Similarly, the measurement region setting unit 13 selects a landmark LB1 on the contour of the face and a landmark LB2 on the nose. In addition, the measurement region setting unit 13 sets auxiliary landmarks b1, b2 and b3 in such a manner that the auxiliary landmarks b1, b2 and b3 equally divide the line segment between the landmark LB1 and the landmark LB2 into four. Note that, for example, the landmarks LB1 and LB2 may be selected from landmarks on the contour of the face and the nose, respectively, that are adjacent to the landmarks LA1 and LA2.

The measurement region setting unit 13 sets, as one measurement region R1, a quadrilateral region surrounded by the auxiliary landmarks a1, b1, b2 and a2. Each of the auxiliary landmarks a1, b1, b2 and a2 is at the coordinates of a vertex of the measurement region R1. Similarly, the measurement region setting unit 13 sets one measurement region R2 surrounded by the auxiliary landmarks a2, b2, b3 and a3, and sets the vertex coordinates of the measurement region R2.

Note that whereas measurement regions fi(k) are set at a portion corresponding to the cheeks in the example explained here, for example, the measurement region setting unit 13 sets measurement regions fi(k) and the vertex coordinates of the measurement regions fi(k) similarly for the other portion of the cheeks, and the portion corresponding to the chin in the skin region sr. Note that although not depicted in FIG. 2C, the measurement region setting unit 13 may set measurement regions fi(k) for the portion corresponding to the forehead of the driver or the portion corresponding to the tip of the nose of the driver in the skin region sr.

Figure 3A:
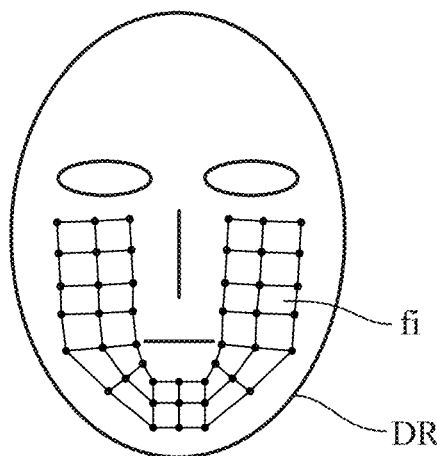
FIG. 3A and FIG. 3B are figures for explaining examples of measurement region setting performed by the measurement region setting unit in the first embodiment.

In this manner, for example as depicted in FIG. 3A, the measurement region setting unit 13 divides the regions corresponding to the left and right cheeks of a driver DR in the skin region represented by the skin region information S(k) in a predetermined manner, and sets the measurement regions fi(k) (i=1, 2, 3, . . . , n). In this case, the measurement regions fi(k) are set in such a manner that the measurement regions fi(k) form a U shape, for example, in the skin region represented by the skin region information S(k).

Figure 3B:
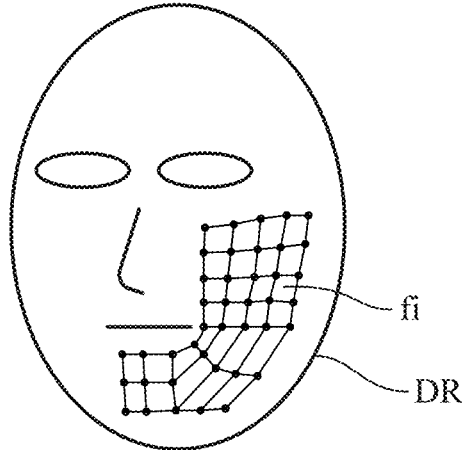

Note that the measurement region setting unit 13 may decide where to set measurement regions as appropriate depending on the orientation of the face of the driver. For example, in a case where the face of the driver is facing slightly rightward relative to the front side, for example as depicted in FIG. 3B, the measurement region setting unit 13 may set measurement regions fi(k) only in the region corresponding to the left cheek of the driver (the region closer to the image-capturing device) in the skin region. In this case, the measurement regions are set in such a manner that the measurement regions form a J shape, for example, in the skin region represented by the skin region information S(k). Note that the measurement region setting unit 13 may determine the orientation of the face of the driver by a known technique. In the following explanation, measurement regions that the measurement region setting unit 13 sets initially for a skin region are also referred to as "initial measurement regions."

In addition, the measurement region setting unit 13 may decide the maximum possible number of measurement regions that may be set in advance from the acquired layout information about the vehicle described above, and a predetermined angle range of the orientation of the face of the driver.

For example, the measurement region setting unit 13 may decide in advance that the maximum number of measurement regions to be set is 28, for example, in a case where the face of the driver DR is facing slightly rightward relative to the front side as depicted in FIG. 3B, and the image-capturing device captured an image of the driver DR diagonally from the front side of the driver DR. Then, the measurement region setting unit 13 may set 28 measurement regions as initial measurement regions for the skin region represented by the skin region information S(k) obtained when the image-capturing device actually captured an image of the driver DR diagonally from the front side.

Similarly, the measurement region setting unit 13 may decide in advance that the maximum number of measurement regions to be set is 40, for example, in a case where the face of the driver DR is facing the front side as depicted in FIG. 3A, and the image-capturing device captured an image of the driver DR from the front side of the driver DR. Then, the measurement region setting unit 13 may set 40 measurement regions as initial measurement regions for the skin region represented by the skin region information S(k) obtained when the image-capturing device actually captured an image of the driver DR from the front side.

After setting the initial measurement regions as described above, the measurement region setting unit 13 calculates the number of pixels included in each of the set initial measurement regions. Then, the measurement region setting unit 13 calculates the ratio of initial measurement regions with the number of pixels which is equal to or greater than a preset reference value in the set plurality of initial measurement regions, and, in a case where the calculated ratio is lower than the threshold, performs measurement region resetting so as to make the ratio equal to or higher than the threshold. Note that details of the measurement region resetting are mentioned later.

The measurement region setting unit 13 outputs the measurement region information R(k) representing the set or reset plurality of measurement regions fi(k) to the luminance signal extracting unit 14.

The luminance signal extracting unit 14 extracts a luminance signal representing a luminance change from each measurement region fi(k) represented by the measurement region information R(k) on the basis of the measurement region information R(k) output from the measurement region setting unit 13.

For example, for each measurement region fi(k) set by the measurement region setting unit 13 on the current frame, the luminance signal extracting unit 14 calculates the average value of luminance values of pixels included in the measurement region. Then, the luminance signal extracting unit 14 sets, as luminance signal information Gi(k), information representing the calculated average value of luminance values of each measurement region. Similarly, for each measurement region fi(k−1) set by the measurement region setting unit 13 on the previous frame which is one frame before the current frame, the luminance signal extracting unit 14 calculates the average value of luminance values of pixels included in the measurement region. Then, the luminance signal extracting unit 14 sets, as luminance signal information Gi(k−1), information representing the calculated average value of luminance values of each measurement region.

Then, the luminance signal extracting unit 14 calculates the difference between the luminance signal information Gi(k) and the luminance signal information Gi(k−1). Specifically, the luminance signal extracting unit 14 calculates the difference between the average values of luminance values of corresponding measurement regions in the luminance signal information Gi(k) and the luminance signal information Gi(k−1). At this time, in a case where either of the luminance signal information Gi(k) and the luminance signal information Gi(k−1) has a measurement region which is not included in the other, the luminance signal extracting unit 14 does not calculate a difference thereof.

Then, the luminance signal extracting unit 14 outputs, to the luminance signal segment generating unit 15, information representing the calculated differences between the luminance signal information Gi(k) and the luminance signal information Gi(k−1) as luminance signal segment information W(t). At this time, the luminance signal extracting unit 14 includes, in the luminance signal segment information W(t), information representing the orientation of the face of the subject on the current frame (k), and information representing the orientation of the face of the subject on the previous frame (k−1).

Here, t represents a number corresponding to the temporal difference between the current frame (k) and the previous frame (k−1). For example, if it is assumed that the luminance signal segment information representing the difference between the luminance signal information Gi(k) and the luminance signal information Gi(k−1) is W(t), the luminance signal segment information representing the difference between luminance signal information Gi(k+1) and the luminance signal information Gi(k) is W(t+1).

Note that in the case explained as an example in the explanation described above, the luminance signal extracting unit 14 uses information representing the calculated average value of luminance values of each measurement region as the luminance signal information Gi(k). However, this is not the sole example, but, for example, the luminance signal extracting unit 14 may use information representing the calculated variance of luminance values of each measurement region as the luminance signal information Gi(k).

The luminance signal segment generating unit 15 continuously accumulates (stores) the luminance signal segment information W(t) output from the luminance signal extracting unit 14 in a storage unit such as a memory until an amount of the information corresponding to a predetermined length of time necessary for estimation of a pulse wave is accumulated. Thereby, the luminance signal segment generating unit 15 generates a time-series luminance signal (luminance signal segment) representing the look of time-series changes of luminance values of each measurement region.

Then, from the generated time-series luminance signals of the measurement regions, the luminance signal segment generating unit 15 selects a time-series luminance signal to be used for estimation of a pulse wave at the pulse wave estimating unit 16 mentioned later. For example, from the generated time-series luminance signals of the measurement regions, the luminance signal segment generating unit 15 selects a time-series luminance signal obtained when the deviation between the orientation of the face on the current frame (k) and previous frame (k−1) of the driver DR included in the luminance signal segment information W(t) and a preset reference face orientation is within a predetermined range (e.g. the range of "−5 degree" to "+5 degrees") as a time-series luminance signal to be used for estimation of a pulse wave of the subject.

A reason why the luminance signal segment generating unit 15 selects a time-series luminance signal in this manner is as follows. That is, basically a pulse wave (pulse) is captured by capturing a luminance change in the same measurement region in pulse wave estimation, but a luminance change can be also caused by factors other than blood flow. In particular, in a case where the orientation of the face of the subject driver DR changes, the direction of incidence of light changes relative to the face of the driver DR, and accordingly the luminance changes significantly. Accordingly, it is desirable if, in pulse wave estimation, luminance values (luminance signals) obtained when the deviation between the orientation of the face and the reference face orientation is significant are not used for estimation of a pulse wave. In view of this, the luminance signal segment generating unit 15 selects a time-series luminance signal to be used for estimation of a pulse wave of the subject by using the orientation of the face of the driver DR described above as a condition.

As segment information X(t), the luminance signal segment generating unit 15 outputs information representing the selected time-series luminance signal to the pulse wave estimating unit 16.

The pulse wave estimating unit 16 estimates a pulse wave of the subject on the basis of the segment information X(t) output from the luminance signal segment generating unit 15. For example, the pulse wave estimating unit 16 adds together the differences between the average values of luminance values of the measurement regions fi(k) included in the segment information X(t) output from the luminance signal segment generating unit 15, and calculates one piece of pulse wave signal information. Then, the pulse wave estimating unit 16 performs the Fourier transform on the calculated pulse wave signal information, and estimates a pulse wave of the subject on the basis of the peak frequency of a frequency power spectrum.

Note that whereas the pulse wave estimating device 1 includes the luminance signal segment generating unit 15 in the example explained in the explanation described above, the luminance signal segment generating unit 15 is not an essential constituent element, and may be omitted. In that case, the pulse wave estimating unit 16 may accumulate (store) the luminance signal segment information W(t) output from the luminance signal extracting unit 14 in the storage unit such as a memory until an amount of the information corresponding to a predetermined length of time necessary for estimation of a pulse wave is accumulated, and estimate a pulse wave of the subject on the basis of the accumulated information.

Figure 4:
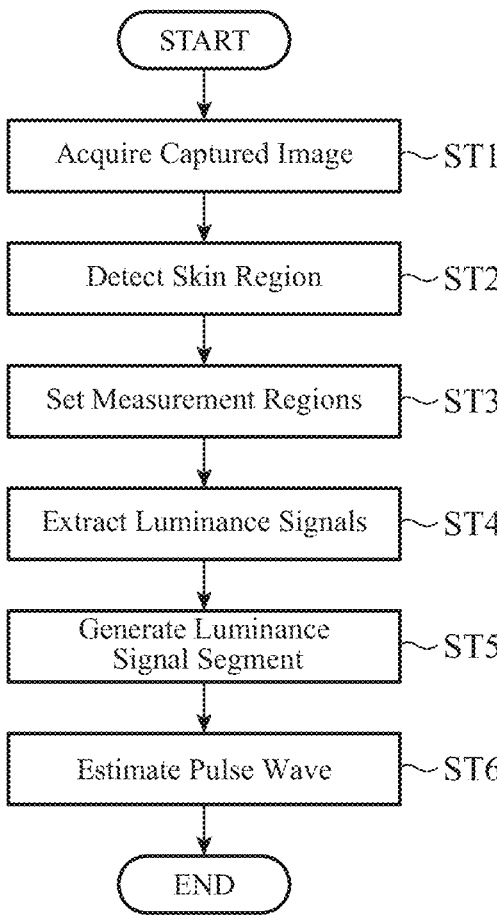
FIG. 4 is a flowchart depicting an example of operations performed by the pulse wave estimating device according to the first embodiment.

Next, an example of operations performed by the pulse wave estimating device 1 depicted in FIG. 1 is explained. FIG. 4 is a flowchart representing an example of operations performed by the pulse wave estimating device 1.

First, the captured image acquiring unit 11 acquires a captured image of the subject driver DR (Step ST1). The captured image acquiring unit 11 outputs the acquired captured image to the skin region detecting unit 12.

Next, the skin region detecting unit 12 detects a skin region on a frame Im(k) included in the captured image acquired by the captured image acquiring unit 11 at Step ST1 (Step ST2). The skin region detecting unit 12 generates the skin region information S(k) representing the detected skin region, and outputs the generated skin region information S(k) to the measurement region setting unit 13 along with the frame Im(k).

Next, on the basis of the frame Im(k), the skin region information S(k) and the vehicle layout information, the measurement region setting unit 13 divides the skin region represented by the skin region information S(k) on the frame Im(k) in a predetermined manner, and sets regions obtained by the division as a plurality of measurement regions for extracting luminance signals representing luminance changes (Step ST3).

Figure 5:
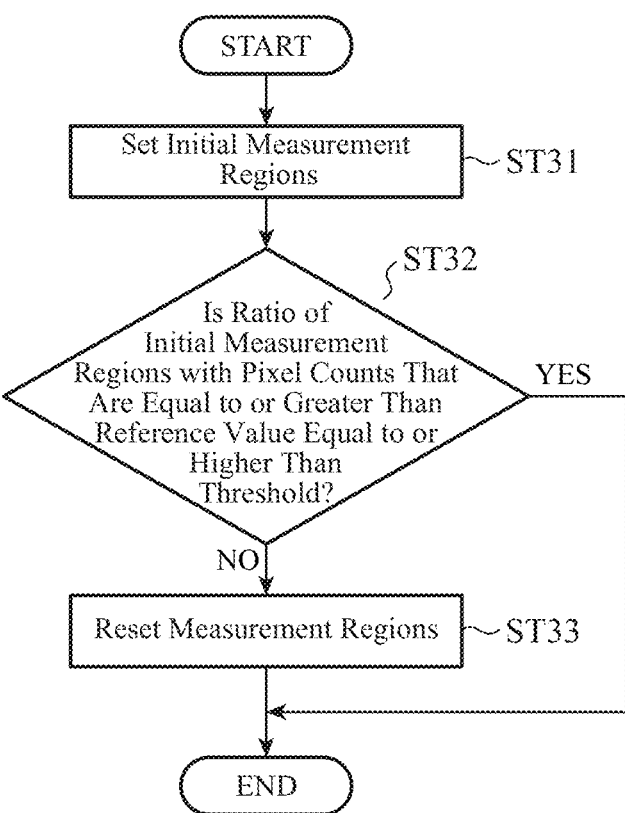
FIG. 5 is a flowchart for explaining details of a process performed by the measurement region setting unit in the first embodiment.

Here, details of the process performed by the measurement region setting unit 13 are explained with reference to a flowchart depicted in FIG. 5.

First, the measurement region setting unit 13 divides the skin region represented by the skin region information S(k) on the frame Im(k) in a predetermined manner, and sets regions obtained by the division as a plurality of measurement regions (initial measurement regions) for extracting luminance signals representing luminance changes (Step ST31).

Next, the measurement region setting unit 13 calculates the number of pixels included in each of the set initial measurement regions. Then, the measurement region setting unit 13 calculates the ratio of initial measurement regions with the number of pixels which is equal to or greater than a preset reference value in the set plurality of initial measurement regions, and assesses whether or not the calculated ratio is equal to or higher than a threshold (Step ST32).

If, as a result of the assessment, the calculated ratio is equal to or higher than the threshold (Step ST32; YES), the measurement region setting unit 13 ends the process. Thereafter, the process returns to Step ST4 depicted in FIG. 4. On the other hand, if the calculated ratio is not equal to or higher than the threshold (Step ST32; NO), the measurement region setting unit 13 performs measurement region resetting so as to make the ratio equal to or higher than the threshold (Step ST33).

Note that the reference value and threshold described above may be set as appropriate, for example, by an administrator of the pulse wave estimating device 1 on the basis of the precision required for pulse wave estimation or the like. For example, the administrator of the pulse wave estimating device 1 increases the reference value and threshold described above to be set, as the precision required for pulse wave estimation increases. For example, in a case where the threshold described above is set to "100%," the measurement region setting unit 13 performs the measurement region resetting if there is even one initial measurement region with a pixel count which is lower than the preset reference value in the set initial measurement regions. In addition, for example, in a case where the threshold described above is set to "50%," the measurement region setting unit 13 does not perform the measurement region resetting if the number of initial measurement regions with the number of pixels which is equal to or greater than the preset reference value is equal to or greater than half of the number of the set initial measurement regions.

For example, the measurement region setting unit 13 performs the measurement region resetting by the following three methods.

(Method 1).

Figure 6:
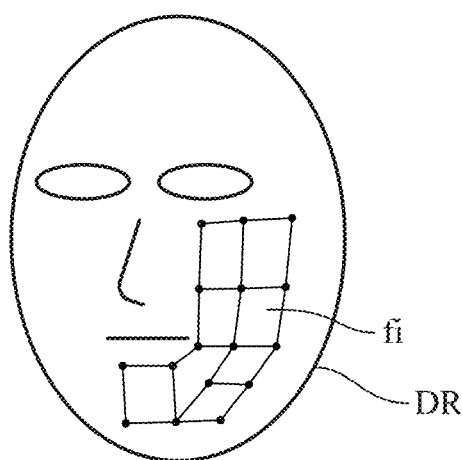
FIG. 6 is a figure for explaining an example of measurement region resetting performed by the measurement region setting unit in the first embodiment.

For example, the measurement region setting unit 13 performs the measurement region resetting by making the number of divisions of the skin region smaller than that at the time of the initial measurement region setting, so as to make the ratio described above equal to or higher than the threshold. For example, if the ratio described above is not equal to or higher than the threshold in a case where 28 initial measurement regions are set as in FIG. 3B, the measurement region setting unit 13 performs the measurement region resetting by reducing the number of division of the skin region to eight as depicted in FIG. 6. In addition, at this time, the measurement region setting unit 13 makes a pixel count per measurement region after the resetting depicted in FIG. 6 greater than a pixel count per measurement region before the resetting depicted in FIG. 3B.

Here, when reducing the number of divisions of the skin region, the measurement region setting unit 13 may reduce the number of divisions of the skin region by merging some of adjacent initial measurement regions in the plurality of initial measurement regions depicted in FIG. 3B. Alternatively, the measurement region setting unit 13 may reset measurement regions by discarding the plurality of initial measurement regions depicted in FIG. 3B, and re-dividing the skin region at a number of division which is smaller than that at the time of the setting of the initial measurement regions.

(Method 2)

For example, the measurement region setting unit 13 performs the measurement region resetting by setting new measurement regions each extending over a predetermined number of adjacent initial measurement regions in the plurality of initial measurement regions, so as to make the ratio described above equal to or higher than the threshold. For example, if the ratio described above is not equal to or higher than the threshold in a case where 28 initial measurement regions are set as in FIG. 3B, as depicted in FIG. 7A to FIG. 7D, the measurement region setting unit 13 performs the measurement region resetting by setting new measurement regions each extending over two or four adjacent initial measurement regions in the 28 initial measurement regions. In this example, thirteen measurement regions from fi(1) to fi(13) are newly set.

In addition, at this time, the thirteen new measurement regions are permitted to overlap each other. For example, the measurement region fi(9) overlaps the measurement regions fi(1) and fi(3), and the measurement region fi(10) overlaps the measurement regions fi(2) and fi(4).

In addition, in this case also, the measurement region setting unit 13 makes a pixel count per measurement region after the resetting depicted in FIG. 7A to FIG. 7D greater than a pixel count per measurement region before the resetting depicted in FIG. 3B.

(Method 3)

For example, the measurement region setting unit 13 may combine the method 1 and the method 2. For example, the measurement region setting unit 13 may perform the measurement region resetting by reducing the number of divisions of the skin region, and also setting new measurement regions each extending over a predetermined number of adjacent measurement regions in a plurality of measurement regions obtained by reducing the number of divisions, so as to make the ratio described above equal to or higher than the threshold. For example, a new measurement region extending over two adjacent measurement regions in the eight measurement regions depicted in FIG. 6 may be set.

The measurement region setting unit 13 performs the measurement region resetting by any of the methods 1 to 3 mentioned above. Thereafter, the process returns to Step ST4 depicted in FIG. 4.

Next, advantageous effects of the pulse wave estimating device 1 according to the first embodiment are explained. By performing the measurement region resetting as described above, the pulse wave estimating device 1 can suppress deterioration of the pulse wave estimation precision as compared to conventional techniques.

For example, in the conventional pulse wave estimation techniques, if the installation layout of an image-capturing device to capture images of the subject driver DR is changed or the image-capturing device itself is replaced, and accordingly the image resolution of captured images of the driver DR deteriorates, the resolving power deteriorates, and the pulse wave estimation precision deteriorates in some cases. In addition, in the conventional pulse wave estimation techniques, also in a case where the driver DR moved the seat of the vehicle back or changed the orientation of the face, and accordingly the face of the driver DR moved away from the image-capturing device, the image resolution of captured images of the driver DR deteriorates, and a similar problem occurs in some cases.

In contrast to this, in a case where the ratio of measurement regions with the number of pixels which is equal to or greater than the preset reference value in a plurality of measurement regions set by the measurement region setting unit 13 is lower than the threshold, the pulse wave estimating device 1 performs the measurement region resetting dynamically so as to make the ratio equal to or higher than the threshold. Thereby, the pulse wave estimating device 1 makes the ratio of measurement regions with the number of pixels which is equal to or greater than the reference value equal to or higher than the threshold after the resetting, suppresses deterioration of the resolving power and suppresses deterioration of the pulse wave estimation precision.

In addition, the pulse wave estimating device 1 achieves also the following advantageous effect in a case where the measurement region setting unit 13 adopts the method 2 described above. For example, in a case where the measurement region setting unit 13 resets measurement regions by reducing the number of divisions of the skin region as in the method 1 described above, if local external light enters some of measurement regions obtained after the resetting undesirably, those measurement regions cannot be used for estimation of a pulse wave, and accordingly there is a possibility that the number of measurement regions that can be used for estimation of a pulse wave decreases, and the robustness deteriorates.

In this regard, in the method 2 described above, the measurement region setting unit 13 resets new measurement regions each extending over a predetermined number of adjacent initial measurement regions while permitting the new measurement regions to overlap each other. Accordingly, it is possible also to ensure there is a sufficient number of measurement regions that can be used for estimation of a pulse wave while ensuring that the measurement regions have sufficient sizes (there are a sufficient number of pixels in each measurement region), and it is possible to suppress deterioration of robustness as compared with the method 1.

In addition, in a case where the measurement region setting unit 13 adopts the method 3 described above, the pulse wave estimating device 1 can make the sizes of measurement regions after the resetting (the numbers of pixels in the measurement regions) greater than in a case where the method 1 or the method 2 is adopted singly, and also can suppress deterioration of robustness which is a problem with the method 1.

Figures 8A, 8B:
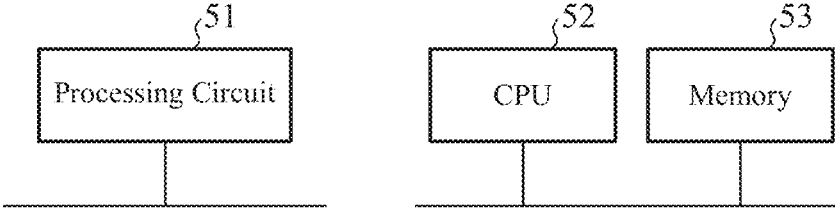
FIG. 8A and FIG. 8B are figures depicting a hardware configuration example of the pulse wave estimating device according to the first embodiment.

Next, a hardware configuration example of the pulse wave estimating device 1 according to the first embodiment is explained with reference to FIG. 8. The respective functions of the captured image acquiring unit 11, the skin region detecting unit 12, the measurement region setting unit 13, the luminance signal extracting unit 14, the luminance signal segment generating unit 15 and the pulse wave estimating unit 16 in the pulse wave estimating device 1 are implemented by a processing circuit. The processing circuit may be dedicated hardware as depicted in FIG. 8A, or may be a Central Processing Unit (CPU; also referred to as a central processor, a processing unit, a computing device, a microprocessor, a microcomputer, a processor or a Digital Signal Processor (DSP)) 52 to execute programs stored in a memory 53 as depicted in FIG. 14B.

In a case where the processing circuit is dedicated hardware, for example, a processing circuit 51 is a single circuit, a composite circuit, a programmed processor, a parallel-programmed processor, an Application Specific Integrated Circuit (ASIC), a Field Programmable Gate Array (FPGA) or a combination of these. Each of the functions of the captured image acquiring unit 11, the skin region detecting unit 12, the measurement region setting unit 13, the luminance signal extracting unit 14, the luminance signal segment generating unit 15 and the pulse wave estimating unit 16 may be implemented by the processing circuit 51 or the functions of the respective units may be collectively implemented by the processing circuit 51.

In a case where the processing circuit is the CPU 52, the functions of the captured image acquiring unit 11, the skin region detecting unit 12, the measurement region setting unit 13, the luminance signal extracting unit 14, the luminance signal segment generating unit 15 and the pulse wave estimating unit 16 are implemented by software, firmware or a combination of software and firmware. Software and firmware are written as programs, and stored in the memory 53. The processing circuit implements the function of each unit by reading out and executing the programs stored on the memory 53. That is, the pulse wave estimating device 1 includes a memory for storing the programs, execution of which by the processing circuit results in execution of each step depicted in FIG. 4, for example. In addition, these programs can also be said to be programs for causing a computer to execute procedures and methods of the captured image acquiring unit 11, the skin region detecting unit 12, the measurement region setting unit 13, the luminance signal extracting unit 14, the luminance signal segment generating unit 15 and the pulse wave estimating unit 16. Here, for example, a non-volatile or volatile semiconductor memory such as a Random Access Memory (RAM), a Read Only Memory (ROM), a flash memory, an Erasable Programmable ROM (EPROM) or an Electrically EPROM (EEPROM), a magnetic disk, a flexible disc, an optical disc, a compact disc, a mini disc, a Digital Versatile Disc (DVD) or the like may be used as the memory 53.

Note that some of the respective functions of the captured image acquiring unit 11, the skin region detecting unit 12, the measurement region setting unit 13, the luminance signal extracting unit 14, the luminance signal segment generating unit 15 and the pulse wave estimating unit 16 may be implemented by dedicated hardware, and the others may be implemented by software or firmware. For example, it is possible to implement the function of the captured image acquiring unit 11 by using the processing circuit as dedicated hardware, and implement the functions of the skin region detecting unit 12, the measurement region setting unit 13, the luminance signal extracting unit 14, the luminance signal segment generating unit 15 and the pulse wave estimating unit 16 by causing the processing circuit to read out and execute programs stored in the memory 53.

In this manner, the processing circuit can implement the respective functions mentioned above by hardware, software, firmware or a combination of these.

As mentioned above, according to the first embodiment, the pulse wave estimating device 1 includes: the captured image acquiring unit 11 to acquire a captured image of a human; the skin region detecting unit 12 to detect a skin region of the human on the captured image; the measurement region setting unit 13 to set, as a plurality of measurement regions for extracting luminance signals representing luminance changes, regions formed by dividing the skin region on the captured image in a predetermined manner; the luminance signal extracting unit 14 to extract the luminance signals on the basis of the luminance changes in the measurement regions on the captured image; and the pulse wave estimating unit 16 to estimate a pulse wave of the human on the basis of the extracted luminance signals, in which the measurement region setting unit 13 performs measurement region resetting so as to make a ratio of measurement regions with the number of pixels which is equal to or greater than a preset reference value in the set plurality of measurement regions equal to or higher than a threshold in a case where the ratio is lower than the threshold. Thereby, it becomes possible for the pulse wave estimating device 1 according to the first embodiment to suppress deterioration of the pulse wave estimation precision.

In addition, the measurement region setting unit 13 performs the measurement region resetting by reducing the number of divisions of the skin region on the captured image in a case where the ratio described above is lower than the threshold. Thereby, the pulse wave estimating device 1 according to the first embodiment can simply reset measurement regions.

In addition, the measurement region setting unit 13 performs the measurement region resetting by setting a new measurement region extending over a predetermined number of adjacent measurement regions in the set plurality of measurement regions in a case where the ratio described above is lower than the threshold. Thereby, the pulse wave estimating device 1 according to the first embodiment can simply reset measurement regions.

In addition, a plurality of the new measurement regions described above can be set, and mutually overlapping measurement regions can be set as the new measurement regions. Thereby, the pulse wave estimating device 1 according to the first embodiment can ensure also that there is a sufficient number of measurement regions that can be used for estimation of a pulse wave, while ensuring that the measurement regions have sufficient sizes.

In addition, the measurement region setting unit 13 performs the measurement region resetting by reducing the number of divisions of the skin region on the captured image, and also setting a new measurement region extending over a predetermined number of adjacent measurement regions in a plurality of measurement regions obtained by reducing the number of divisions, in a case where the ratio described above is lower than the threshold. Thereby, the pulse wave estimating device 1 according to the first embodiment can increase the sizes of measurement regions after the resetting.

In addition, the measurement region setting unit 13 makes a pixel count per measurement region after the resetting greater than the number of pixels per measurement region before the resetting. Thereby, the pulse wave estimating device 1 according to the first embodiment can suppress deterioration of the resolving power, and suppress deterioration of the pulse wave estimation precision.

In addition, the pulse wave estimating device 1 includes the luminance signal segment generating unit 15 to select a luminance signal to be used for the estimation of the pulse wave of the human in the luminance signals extracted by the luminance signal extracting unit 14, in which the pulse wave estimating unit 16 estimates the pulse wave of the human on the basis of the luminance signal selected by the luminance signal segment generating unit 15. Thereby, the pulse wave estimating device 1 according to the first embodiment can suppress deterioration of the pulse wave estimation precision effectively.

In addition, the luminance signal segment generating unit 15 selects, as the luminance signal to be used for the estimation of the pulse wave of the human, a luminance signal in the luminance signals extracted by the luminance signal extracting unit 14 that has been extracted when the deviation between the orientation of the face of the human and a preset reference face orientation is within a predetermined range. Thereby, the pulse wave estimating device 1 according to the first embodiment can select a time-series luminance signal to be used for estimation of a pulse wave by using the orientation of the face of the human as a condition.

Although a preferred embodiment and the like have been explained in detail thus far, the embodiment and the like mentioned above do not limit the present disclosure, and various manners of modification and replacement are possible about the embodiment and the like mentioned above without departing from the scope described in claims.

Hereinbelow, several aspects of the present disclosure are described collectively as notes.

(Note 1)

A pulse wave estimating device including:

a captured image acquiring unit to acquire a captured image of a human;

a skin region detecting unit to detect a skin region of the human on the captured image;

a measurement region setting unit to set, as a plurality of measurement regions for extracting luminance signals representing luminance changes, regions formed by dividing the skin region on the captured image in a predetermined manner;

a luminance signal extracting unit to extract the luminance signals on a basis of the luminance changes in the measurement regions on the captured image; and a pulse wave estimating unit to estimate a pulse wave of the human on a basis of the extracted luminance signals, in which the measurement region setting unit performs measurement region resetting, when a ratio of measurement regions, in which a number of pixels is equal to or greater than a preset reference value among the set plurality of measurement regions, is lower than a threshold, in such a manner as to make the ratio of measurement regions equal to or higher than the threshold.

(Note 2)

The pulse wave estimating device according to note 1, in which the measurement region setting unit performs the measurement region resetting by reducing the number of divisions of the skin region on the captured image in a case where the ratio is lower than the threshold.

(Note 3)

The pulse wave estimating device according to note 1, in which the measurement region setting unit performs the measurement region resetting by setting a new measurement region extending over a predetermined number of adjacent measurement regions in the set plurality of measurement regions in a case where the ratio is lower than the threshold.

(Note 4)

The pulse wave estimating device according to note 3, in which a plurality of the new measurement regions can be set, and mutually overlapping measurement regions can be set as the new measurement regions.

(Note 5)

The pulse wave estimating device according to note 1, in which the measurement region setting unit performs the measurement region resetting by reducing the number of divisions of the skin region on the captured image, and also setting a new measurement region extending over a predetermined number of adjacent measurement regions in the plurality of measurement regions obtained by reducing the number of divisions, in a case where the ratio is lower than the threshold.

(Note 6)

The pulse wave estimating device according to any one of notes 1 to 5, in which the measurement region setting unit makes the number of pixels per measurement region after the resetting greater than the number of pixels per measurement region before the resetting.

(Note 7)

The pulse wave estimating device according to any one of notes 1 to 6, including a luminance signal segment generating unit to select a luminance signal to be used for the estimation of the pulse wave of the human from among the luminance signals extracted by the luminance signal extracting unit, in which the pulse wave estimating unit estimates the pulse wave of the human on a basis of the luminance signal selected by the luminance signal segment generating unit.

(Note 8)

The pulse wave estimating device according to note 7, in which the luminance signal segment generating unit selects, as the luminance signal to be used for the estimation of the pulse wave of the human, a luminance signal, from among the luminance signals extracted by the luminance signal extracting unit, which has been extracted when a deviation between an orientation of a face of the human and a preset reference face orientation is within a predetermined range.

(Note 9)

A pulse wave estimation method performed by a pulse wave estimating device, the pulse wave estimation method comprising:

acquiring, by a captured image acquiring unit, a captured image of a human;

detecting, by a skin region detecting unit, a skin region of the human on the captured image;

setting, by a measurement region setting unit, regions formed by dividing the skin region on the captured image in a predetermined manner, as a plurality of measurement regions for extracting luminance signals representing luminance changes;

extracting, by a luminance signal extracting unit, the luminance signals on a basis of the luminance changes in the measurement regions on the captured image;

estimating, by a pulse wave estimating unit, a pulse wave of the human on a basis of the extracted luminance signals; and performing, by the measurement region setting unit, measurement region resetting when a ratio of measurement regions, in which a number of pixels is equal to or greater than a preset reference value among the set plurality of measurement regions, is lower than a threshold, in such a manner as to make the ratio of measurement regions equal to or higher than the threshold.

INDUSTRIAL APPLICABILITY

The present disclosure enables suppression of deterioration of pulse wave estimation precision, and is suited for being used for a pulse wave estimating device.

REFERENCE SIGNS LIST

1: pulse wave estimating device, 11: captured image acquiring unit, 12: skin region detecting unit, 13: measurement region setting unit, 14: luminance signal extracting unit, 15: luminance signal segment generating unit, 16: pulse wave estimating unit, 51: processing circuit, 52: CPU, 53: memory, a1 to a3: auxiliary landmark, b1 to b3: auxiliary landmark, DR: driver, fi: measurement region, LA1 to LA2: landmark, LB1 to LB2: landmark, sr: skin region

The invention claimed is:

1. A pulse wave estimating device mounted on a vehicle, the pulse wave estimating device comprising:

processing circuitry configured to acquire a captured image of a human that is a driver of the vehicle;

detect a skin region of the human on the captured image;

set, as a plurality of measurement regions for extracting luminance signals representing luminance changes, regions formed by dividing the skin region on the captured image in a predetermined manner;

perform measurement region resetting on the plurality of measurement regions, when a ratio of measurement regions, in which a number of pixels is equal to or greater than a preset reference value among the set plurality of measurement regions, is lower than a threshold, in such a manner as to make the ratio of measurement regions equal to or higher than the threshold;

extract the luminance signals on a basis of the luminance changes in the set measurement regions or the reset measurement regions on the captured image; and estimate a pulse wave of the human on a basis of luminance signal segment information from the extracted luminance signals according to the set plurality of measurement regions or the reset plurality of measurement regions, wherein the estimated pulse wave based on the set plurality of measurement regions or the reset plurality of measurement regions suppresses deterioration of accuracy of the estimated pulse wave caused by movement of the human.

2. The pulse wave estimating device according to claim 1, wherein the processing circuitry performs the measurement region resetting by reducing the number of divisions of the skin region on the captured image in a case where the ratio is lower than the threshold.

3. The pulse wave estimating device according to claim 1, wherein the processing circuitry performs the measurement region resetting by setting at least one new measurement region extending over a predetermined number of adjacent measurement regions in the set plurality of measurement regions in a case where the ratio is lower than the threshold.

4. The pulse wave estimating device according to claim 3, wherein the at least one new measurement region includes a plurality of new measurement regions which can be overlapped with each other.

5. The pulse wave estimating device according to claim 1, wherein the processing circuitry performs the measurement region resetting by reducing the number of divisions of the skin region on the captured image, and also setting at least one new measurement region extending over a predetermined number of adjacent measurement regions in the plurality of measurement regions obtained by reducing the number of divisions, in a case where the ratio is lower than the threshold.

6. The pulse wave estimating device according to claim 1, wherein the processing circuitry makes the number of pixels per measurement region after the resetting greater than the number of pixels per measurement region before the resetting.

7. The pulse wave estimating device according to claim 1, wherein the processing circuitry is configured to select a luminance signal to be used for the estimation of the pulse wave of the human from among the extracted luminance signals, and estimate the pulse wave of the human on a basis of the selected luminance signal.

8. The pulse wave estimating device according to claim 7, wherein the processing circuitry selects, as the luminance signal to be used for the estimation of the pulse wave of the human, a luminance signal, from among the extracted luminance signals, which has been extracted when a deviation between an orientation of a face of the human and a preset reference face orientation is within a predetermined range.

9. A pulse wave estimation method performed by a pulse wave estimating device mounted on a vehicle, the pulse wave estimation method comprising:

acquiring a captured image of a human that is a driver of the vehicle;

detecting a skin region of the human on the captured image; setting regions formed by dividing the skin region on the captured image in a predetermined manner, as a plurality of measurement regions for extracting luminance signals representing luminance changes;

performing measurement region resetting on the plurality of measurement regions, when a ratio of measurement regions, in which a number of pixels is equal to or greater than a preset reference value among the set plurality of measurement regions, is lower than a threshold, in such a manner as to make the ratio of measurement regions equal to or higher than the threshold;

extracting the luminance signals on a basis of the luminance changes in the set measurement regions or the reset measurement regions on the captured image; and estimating a pulse wave of the human on a basis of luminance signal segment information from the extracted luminance signals according to the set plurality of measurement regions or the reset plurality of measurement regions, wherein the estimated pulse wave based on the set plurality of measurement regions or the reset plurality of measurement regions suppresses deterioration of accuracy of the estimated pulse wave caused by movement of the human.

* * * * *